(12) United States Patent
Nishioka

(10) Patent No.: US 7,148,012 B2
(45) Date of Patent: Dec. 12, 2006

(54) THERAPEUTIC AGENT FOR FIBROMYALGIA

(75) Inventor: Kusuki Nishioka, Shibuya-ku (JP)

(73) Assignees: Nippon Zoki Pharmaceutical Co., Ltd., Osaka (JP); Argenes, Inc., Tokyo (JP)

( * ) Notice: Subject to any disclaimer, the term of this patent is extended or adjusted under 35 U.S.C. 154(b) by 0 days.

(21) Appl. No.: 10/532,792

(22) PCT Filed: Oct. 31, 2003

(86) PCT No.: PCT/JP03/13999

§ 371 (c)(1),
(2), (4) Date: Apr. 25, 2005

(87) PCT Pub. No.: WO2004/039383

PCT Pub. Date: May 13, 2004

(65) Prior Publication Data

US 2006/0051376 A1    Mar. 9, 2006

(30) Foreign Application Priority Data

Oct. 31, 2002   (JP)   ............... 2002-317011

(51) Int. Cl.
*C12Q 1/68* (2006.01)
(52) U.S. Cl. ............................. 435/6; 435/5
(58) Field of Classification Search ............ 435/6, 435/5; 424/204.1
See application file for complete search history.

(56) References Cited

U.S. PATENT DOCUMENTS 5,057,324 A * 10/1991 Shibayama et al. ......... 424/520
6,165,515 A    12/2000 Matsuyama et al.

FOREIGN PATENT DOCUMENTS

| EP | 0 348 353 A2 | 12/1989 |
| EP | 0 645 142 A1 | 3/1995 |
| EP | 0 852 950 B1 | 7/1998 |
| EP | 0 916 344 A2 | 5/1999 |
| EP | 0 953 352 A1 | 11/1999 |
| EP | 1 038 529 A2 | 9/2000 |
| JP | A 53-101515 | 9/1978 |
| JP | A 55-87724 | 7/1980 |
| JP | B 63-39572 | 8/1988 |
| JP | A 1-265028 | 10/1989 |
| JP | A 1-319422 | 12/1989 |
| JP | A 2-28119 | 1/1990 |
| JP | A 7-97336 | 4/1995 |
| JP | A 8-291077 | 11/1996 |
| JP | B 2594222 | 12/1996 |
| JP | A 10-194978 | 7/1998 |
| JP | A 11-80005 | 3/1999 |
| JP | A 11-139977 | 5/1999 |
| JP | A 2000-16942 | 1/2000 |
| JP | A 2000-336034 | 12/2000 |
| JP | A 2001-58950 | 3/2001 |
| WO | WO 01/68643 A2 | 9/2001 |

OTHER PUBLICATIONS

Matsuoka et al, Nippon Yakurigaku Zasshi, 1987, vol. 90, No. 1, pp. 67-71, abstract only.*
Yoshi et al, Int. J. Immunopharmacology, 1995, vol. 17, No. 11, pp. 879-886.*
"Drugs in Japan", ethical Drugs[(25th edition), edited by Japan Pharmaceutical Information Center: published by Jino, Inc. (2002)], pp. 2379-2381, with concise explanation.
"Rheumatism", Apr. 2003, vol. 4, No. 2, p. 331, W 51-6-O/P, with translation.

* cited by examiner

Primary Examiner—Ali R. Salimi
(74) Attorney, Agent, or Firm—Oliff & Berridge, PLC

(57) ABSTRACT

A therapeutic agent for fibromyalgia containing an extract from inflamed tissue inoculated with vaccinia virus as an active ingredient, use of the extract from inflamed tissue inoculated with vaccinia virus as the active ingredient for producing a medicinal composition for treating fibromyalgia, and a method of treating fibromyalgia which comprises administering a medicinal composition containing the extract from inflamed tissue inoculated with vaccinia virus as the active ingredient to a patient. The therapeutic agent containing the extract from inflamed tissue inoculated with vaccinia virus as the active ingredient is a novel therapeutic agent for fibromyalgia, no efficacious therapeutic agent for which has been known heretofore. Moreover, it is very useful as an effective drug having high safety with scarcely any side effects.

5 Claims, No Drawings

THERAPEUTIC AGENT FOR FIBROMYALGIA

TECHNICAL FIELD

The present invention relates to a novel medicinal application of an extract from inflamed tissue inoculated with vaccinia virus, and more particularly, relates to a therapeutic agent for fibromyalgia including an extract from inflamed tissue inoculated with vaccinia virus as an active ingredient, use of the extract from inflamed tissue inoculated with vaccinia virus as the active ingredient for producing a medicinal composition for treating fibromyalgia, and a method of treating fibromyalgia which comprises administering a medicinal composition including the extract from inflamed tissue inoculated with vaccinia virus as the active ingredient to a patient.

BACKGROUND ART

Fibromyalgia is a syndrome characterized by chronic and intense generalized pain, or widespread chronic pain over portions of the body; the pain is not limited to muscle tissue and may also be experienced in the skin. In fibromyalgia, such generalized chronic pain is often accompanied by symptoms including fatigue, malaise, depression, anxiety, muscle tightness in the morning, muscle stiffness and sleep disorders. Other accompanying symptoms also include headaches, facial pain, cognitive impairment (memory lapses, loss of concentration), gastrointestinal complaints (visceral pain, digestive system disorders, flatulency), frequent urination, diarrhea, constipation and dysmenorrhea.

It has been reported that 3.4% of women and 0.5% of men in the U.S. general population suffer from fibromyalgia. Moreover, fibromyalgia occurs more often in women generally between 25 and 50 years of age, with women accounting for approximately 80% of all patients. The prevalence rate in Japan are believed to be almost identical to the U.S. Although fibromyalgia has diverse subjective symptoms, objective findings have found few symptoms aside from a characteristic generalized tenderness. Even various immunological, virological and endocrinologic examinations as well as pathological examinations of myalgic regions, in addition to imaging examinations such as MRI and CT, have found almost no abnormalities. For example, although edemas do not occur as with rheumatoid arthritis and a blood index indicating a degree of inflammation, i.e., sedimentation or CRP, is within a normal range, patients complain of widespread pain covering the extremities and trunk.

Classification criteria put forward by the American College of Rheumatology in 1990 are currently used worldwide to diagnosis fibromyalgia. A diagnosis of fibromyalgia is made according to the following criteria: if pain must have been present for at least three months in all five regions of above the waist, below the waist, in the left side of the body, in the right side of the body, and also in the spinal and sternal region; or if pain must have been present in 11 or more sites of the 18 specified tender points when the palpation should be performed with an gentle force of 4 kg.

At present, the causes and mechanisms triggering the onset of fibromyalgia are not known, but are believed to include psychological factors brought on by stress or the like, viral infections, heredity, and immune and neural transmitter disorders. Fibromyalgia is a condition vastly different from many general painful conditions brought on by nociceptive stimulus, which damages or may possibly damage tissue, and no related pathological findings are observed on the pain regions.

Most anti-inflammatory analgesics such as non-steriodal anti-inflammatory drugs (NSAIDs), which are widely used for treating pain in general, are not very effective as treatment for fibromyalgia. Furthermore, various drugs including muscle relaxants, opioid analgesics and antianxiety agents have undergone trial use, but drug efficacy differs greatly among individuals and thus no prominent effect has been recognized. Consequently, as a current treatment of fibromyalgia, the drug therapy with antidepressants, the combined administration of antidepressants and NSAIDs, the administration of local anesthetics or steroids to painful sites, massages, therapeutic exercise, sleep therapy and the like are merely performed. However, the curative effects of all the therapeutic agents and methods differ greatly among individuals and have not been established as methods of the treatment, partly due to the fact that the cause of fibromyalgia has yet to be determined.

As explained above, given that the causes and mechanisms triggering the onset of fibromyalgia are not clear at present, and no drug has been found to demonstrate a prominent curative effect, medical facilities are in great need of a highly safe and effective therapeutic agent.

Thus, it is an object of the present invention to provide a highly safe and effective therapeutic agent for treatment of fibromyalgia, for which there is no efficacious medicine at present.

DISCLOSURE OF INVENTION

As a result of administering a preparation containing an extract from inflamed tissue inoculated with vaccinia virus as an active ingredient to patients who had been diagnosed with fibromyalgia, and for whom existing medicines such as anti-inflammatory analgesics and antidepressants had shown no effect, the inventor discovered that the preparation had a prominent curative effect on fibromyalgia.

Accordingly, the present invention relates to a therapeutic agent for fibromyalgia containing an extract from inflamed tissue inoculated with vaccinia virus as an active ingredient.

Moreover, the present invention relates to use of an extract from inflamed tissue inoculated with vaccinia virus as an active ingredient for producing a medicinal composition for treating fibromyalgia.

Furthermore, the present invention relates to a method of treating fibromyalgia which comprises administering a medicinal composition including an extract from inflamed tissue inoculated with vaccinia virus as an active ingredient to a patient.

BEST MODE FOR CARRYING OUT THE INVENTION

It is known that living organisms produce various biofunction-regulating substances to defend and normalize the organism against invasions of viruses or the like from outside and progressions of internal diseases. There are various reports regarding biofunction-regulating substances that are produced in inflamed tissue inoculated with vaccinia virus, and production methods for extracting the substances from the diseased tissue, as well as the relevant pharmacological activity (such as Japanese Patent Publication No. S63-39572 and Japanese Patent No. 2594222).

However, there are no publications or reports relating to medical applications effective in the treatment of fibromyalgia. Disclosed pharmacological activity regarding extracts from inflamed tissue inoculated with vaccinia virus includes the following: analgesic, sedative, antistress and antiallergic actions (refer to Japanese Patent Laid-Open Publication No. S53-101515); immune stimulation, anticancer and cirrhosis inhibition actions (refer to Japanese Patent Laid-Open Publication No. S55-87724, pages 3, 5 and 6 in particular); a curative effect for idiopathic thrombocytopenic purpura (refer to Japanese Patent Laid-Open Publication No. H01-265028, pages 1 and 2 in particular); curative effects for post-herpetic neuralgia, cerebral edema, dementia, spinocerebellar degeneration and the like (refer to Japanese Patent Laid-Open Publication No. H01-319422, pages 3 and 4 in particular); curative effects for Raynaud's disease, diabetic neuropathy, sequelae of subacute myelo-optic neuropathy and the like (refer to Japanese Patent Laid-Open Publication No. H02-28119, page 3 in particular); kallikrein production inhibition and peripheral circulatory disturbance amelioration actions (refer to Japanese Patent Laid-Open Publication No. H07-97336, page 4 in particular); bone atrophy amelioration action (refer to Japanese Patent Laid-Open Publication No. H08-291077); nitric oxide production inhibition action effective in the treatment of septicemia and endotoxin shock (refer to Japanese Patent Laid-Open Publication No. H10-194978); a curative effect for osteoporosis (refer to Japanese Patent Laid-Open Publication No. H11-80005, pages 2 and 3 in particular); a curative effect for AIDS based upon inhibition actions for Nef action and chemokine production (refer to Japanese Patent Laid-Open Publication No. H11-139977 and Japanese Patent Laid-Open Publication No. 2000-336034, pages 2 and 3 in particular); and a curative effect for ischemic diseases such as cerebral infarctions (refer to Japanese Patent Laid-Open Publication No. 2000-16942).

An extract from inflamed tissue inoculated with vaccinia virus can be obtained by inoculating an animal with vaccinia virus, finely cutting and crushing tissue, adding an extracting medium thereto and removing tissue fragments, after which deproteinization is performed; the deproteinized solution is adsorbed by an adsorbent and then the adsorbed component is extracted. An extract isolated from inflamed tissue inoculated with vaccinia virus can be produced, for example, according to the following process.

(a) Cutaneous tissues or the like are collected from rabbits, mice, etc. inoculated with vaccinia virus, and the finely cut tissue is crushed. An extracting medium such as water, phenol water, saline or phenol-added glycerin water is added, and then an extracted fluid (filtrate or supernatant) is obtained by filtration or centrifugation.

(b) The pH of the extracted fluid is made acidic and it is heated for deproteinization. The deproteinized solution is subsequently made alkaline and heated, after which it undergoes filtration or centrifugation.

(c) The obtained filtrate or supernatant is made acidic, then adsorbed by an adsorbent such as activated carbon or kaolin.

(d) An extracting solvent such as water is added to the adsorbent, the pH is made alkaline and the adsorbed component is eluted, thereby obtaining an extract from inflamed tissue inoculated with vaccinia virus. Thereafter, the eluate can be suitably freeze-dried or evaporated to dryness under reduced pressure to make dried materials.

A pharmaceutical preparation of an extract isolated from inflamed cutaneous tissue of rabbits inoculated with vaccinia virus is used in practice. As described in pages 2379 to 2381 of *Drugs in Japan: Ethical Drugs* [(25th edition), edited by Japan Pharmaceutical Information Center: published by Jiho, Inc. (2002)], the preparation is a drug containing a non-proteinous active substance extracted and isolated from inflamed cutaneous tissue of rabbits inoculated with vaccinia virushas been allowed to use for low back pain, neck-shoulder-arm syndrome, symptomatic neuralgia, periarthritis scapulohumeralis, arthrosis deformans, pruritis caused by dermatoses (eczema, dermatitis and urticaria), allergic rhinitis, sequelae of subacute myelo-optico-neuropathy (coldness, pain and paresthesia/dysesthesia) and post-herpetic neuralgia. Subcutaneous, intramuscular and intravenous injections, as well as tablets, have received manufacturing approval and are sold as ethical drugs.

An active ingredient of the therapeutic agent for fibromyalgia according to the present invention is a non-proteinous biofunction-regulating substance which is extracted from an inflamed tissue inoculated with vaccinia virus as described above. The pharmaceutical preparations of an extract isolated from inflamed cutaneous tissue of rabbits inoculated with vaccinia virus as listed in the above Drugs in Japan: Ethical Drugs have received drug manufacturing approval and is commercially available. Moreover, the various extracts from inflamed tissue inoculated with vaccinia virus described in literature such as the patent publications mentioned above may be employed in the present invention, for which the production method, preferable dose and the like are also explained in the literature.

Oral administration with tablets is the preferred dosage method for patients; however, for cases where symptoms are particularly severe or the like, injections administered intravenously or through instillation may also be used. Due to the diversity of symptoms for fibromyalgia, the dosage form is not limited to oral administration of a drug. The dosage amount should be appropriately set depending on the type of extract from inflamed tissue inoculated with vaccinia virus. According to *Drugs in Japan: Ethical Drugs* (page 2379), the dosage amount recognized for commercial preparations specified as ethical drugs is, in principle, 16 units of neurotropin (NU) per day for oral administrations, and 3.6 to 7.2 NU per day for administrations by injection. However, the dosage amount may be increased or decreased as appropriately depending on the type of condition, severity, personal differences in the patient, dosage method, dosing period or the like.

EXAMPLES

Hereinafter, examples of methods for producing an extract from inflamed tissue inoculated with vaccinia virus, as well as novel pharmacological action, that is, results of a clinical test related to fibromyalgia will be described. It should be noted that although drying under reduced pressure is performed in all final processes of Examples 1–3, such drying procedure is for the purpose of producing a tablet or the like and is not necessary.

Example 1

Skins of a healthy adult rabbit were inoculated with vaccinia virus to cause inflammation. The inflamed cutaneous tissues were aseptically removed and finely cut. Phenol-added glycerin water was subsequently added, and the mixture was ground by a homogenizer to prepare an emulsion. The emulsion was filtered with centrifugation, and the pH of the obtained filtrate was adjusted to 4.8 to 5.5 using hydrochloric acid. The filtrate was then heated to 100° C. using flowing steam and filtrated. After further filtration using a Seitz filter plate, the pH was adjusted to 9.2 using sodium hydroxide, then it was heated to 100° C. and filtrated again. The pH of the filtrate was adjusted to 4.5 using hydrochloric acid, and 1.5% of activated carbon was added. After 1 to 5 hours of stirring, filtration was subsequently performed. Water was added to the activated carbon, and the pH was adjusted to 9.4 to 10 using sodium hydroxide. After 3 to 5 hours of stirring, filtration was performed again. The pH of the filtrate was adjusted to 7.0 to 7.2 using hydrochloric acid, and it was dried under reduced pressured to obtain an extract from inflamed tissue inoculated with vaccinia virus.

Example 2

Skins of a healthy adult rabbit were inoculated with vaccinia virus. The inflamed cutaneous tissues were removed and minced, and phenol water was added. Pressure filtration was subsequently performed, and the pH of the obtained filtrate was adjusted to 5.0 using hydrochloric acid. Heat treatment was then performed for 30 minutes at 90 to 100° C. After deproteinization by filtration, the pH was adjusted to 9.0 using sodium hydroxide. Further the solution was heated for 15 minutes at 90 to 100° C. and subsequently filtrated. The pH of the filtrate was adjusted to approximately 4.5 using hydrochloric acid, and 2% of activated carbon was added. After 2 hours of stirring, centrifugation was performed. Water was added to the collected activated carbon, and the pH was adjusted to 10 using sodium hydroxide. After 1.5 hours of stirring at 60° C., centrifugation was performed again. Water was added to the collected activated carbon, and the pH was adjusted to 11 using sodium hydroxide again. After 1.5 hours of stirring at 60° C., centrifugation was once more performed. The supernatants were neutralized with hydrochloric acid, and drying under reduced pressure was performed to obtain an extract from inflamed tissue inoculated with vaccinia virus.

Example 3

Skins of a healthy adult rabbit were inoculated with vaccinia virus to activate the tissues. The activated cutaneous tissues were aseptically removed and minced. Water was subsequently added, and the mixture was ground by a homogenizer to prepare an emulsion. Pressure filtration was performed next, and the pH of the obtained filtrate was adjusted to 5.0 using hydrochloric acid. The filtrate was then heated at 100° C. using flowing steam. After deproteinization by filtration, the pH was adjusted to 9.1 using sodium hydroxide. Further the solution was heated at 100° C. and subsequently filtrated. The pH of the filtrate was adjusted to 4.1 using hydrochloric acid, and 2% of activated carbon was added. After 2 hours of stirring, filtration was performed. 5.5% of activated carbon was further added to the filtrate. After 2 hours of stirring, filtration was performed again. Water was added to the initially filtrated activated carbon, and the pH was adjusted to 9.9 using sodium hydroxide. After 1.5 hours of stirring at 60° C., filtration was performed again. Water was added to the initial and subsequently added activated carbon, and the pH was adjusted to 10.9 using sodium hydroxide. Following 1.5 hours of stirring, filtration was performed again. After combination with the both filtrates, and the solution was neutralized with hydrochloric acid, and desalted by electrodialysis using a membrane with a molecular weight of 100. The solution was dried under reduced pressured to obtain an extract from inflamed tissue inoculated with vaccinia virus.

Example 4

L-cells (mouse sarcoma cells) were subcutaneously implanted in C3H mouse. The same area was inoculated with vaccinia virus after 10 days, and areas suffering from tumor inflammation were excised after another 5 days. Following mincing of 100 g of the excised tissue, buffered 70% glycerin solution with a pH of 7.0 was added. Grinding was performed with a Waring blender, and freeze-thawing operations were carried out 3 times. The ground emulsion was then centrifuged for 1 hour at 2000×g. After precipitates were removed, the pH of the supernatant was adjusted to 5.0. The supernatant was then heated to 100° C. and filtrated. The pH of the filtrate was adjusted to 9.0, after which it was heated to 100° C. again and filtrated to remove insoluble matters. After cooling, the pH of the filtrate was adjusted to 4.5 and it was passed through a column filled with activated carbon. The column was washed with distilled water and eluted with N/25 ammonia water. The eluate was neutralized with hydrochloric acid to obtain an extract from inflamed tissue inoculated with vaccinia virus.

Clinical Test

Eight patients were administered with a pharmaceutical preparation (product name: Neurotropin™ Tablet) including an extract isolated from inflamed cutaneous tissue of rabbits inoculated with vaccinia virus. These patients had been diagnosed with fibromyalgia in accordance with the classification criteria established by the American College of Rheumatology mentioned above, and all various types of drug therapy including local dosing of steroids, antidepressants and anti-inflammatory analgesics showed no effect. The daily dosage amount was four tablets, each containing 4.0 neurotropin units, which were orally administered twice in the morning and evening for 2 to 4 weeks. With pain prior to drug administration regarded as "10" for a reference, an evaluation of efficacy was determined through patient evaluation (VAS [Visual Analogue Scale] evaluation) hearings to discern the extent to which pain was alleviated after administration. The clinical results are shown in Table 1, and the clinical efficacy of the preparation is summarized in Table 2.

TABLE 1

| No. | Sex | Age | Pre-dosage pain | Post-dosage pain | Efficacy evaluation |
| --- | --- | --- | --- | --- | --- |
| 1 | Male | 64 | 10 | 3 | More effective |
| 2 | Female | 62 | 10 | 2 | Very effective |
| 3 | Female | 67 | 10 | 8 | No effect |
| 4 | Female | 52 | 10 | 2 | Very effective |
| 5 | Female | 48 | 10 | 2 | Very effective |
| 6 | Female | 49 | 10 | 3 | More effective |
| 7 | Female | 69 | 10 | 8 | No effect |
| 8 | Female | 55 | 10 | 8 | No effect |

TABLE 2

| Efficacy evaluation | Total (%) |
| --- | --- |
| Very effective (reduced to 2 or below) | 3 (37.5%) |
| More effective (reduced to 3 or 4) | 2 (25.0%) |
| Effective (reduced to 5 to 7) | 0 |
| No effect (8 or above) | 3 (37.5%) |

Among patients for which the preparation was shown effective in the above clinical testing, accompanying symptoms including fatigue, malaise, depression, anxiety, muscle tightness in the morning, muscle stiffness and sleep disorders were also ameliorated along with predominant symptoms, and patient QOL (Quality of Life) was significantly improved.

INDUSTRIAL APPLICABILITY

As evident in the above clinical test results, an extract from inflamed tissue inoculated with vaccinia virus according to the present invention exhibited a prominent curative effect for fibromyalgia. It should be particularly noted that an improving effect on the condition was recognized in patients who had undergone all other available drug therapies, to no effect, prior to the above clinical testing.

No other drug heretofore has demonstrated such efficacy, and no drug is known to have undergone clinical testing in order to obtain the above effect. Few ordinary anti-inflammatory analgesics such as non-steriodal anti-inflammatory drugs (NSAIDs) have any effect on fibromyalgia; and although antidepressants are often prescribed, there are also problems from side effects or the like. Thus, a drug that may be safely used with few side effects is desired. The drug according to the present invention is a novel therapeutic agent for fibromyalgia, no therapeutic agent for which has been known heretofore. Moreover, it is a highly safe and extremely effective drug with scarcely any side effects.

The invention claimed is:

1. A method of treating fibromyalgia comprising:
  administering to a patient a medicinal composition that comprises, as an active ingredient, an extract from inflamed tissue inoculated with vaccinia virus.

2. The method of treating fibromyalgia according to claim 1, wherein the inflamed tissue is cutaneous tissue.

3. The method of treating fibromyalgia according to claim 2, wherein the inflamed tissue is inflamed cutaneous tissue of rabbits.

4. The method of treating fibromyalgia according to claim 1, wherein the medicinal composition is an injectable preparation.

5. The method of treating fibromyalgia according to claim 1, wherein the medicinal composition is an oral preparation.

* * * * *